United States Patent
Sergeant et al.

(10) Patent No.: US 10,017,476 B2
(45) Date of Patent: Jul. 10, 2018

(54) 1,4-BIS(3-AMINOPROPYL)PIPERAZINE DERIVATIVE AND ITS USE

(71) Applicants: INSERM (Institut National de la Sante et de la Research Medicale), Paris (FR); CENTRE HOSPITALIER REGIONAL ET UNIVERSITAIRE DE LILLE (CHRU), Lille (FR); UNIVERSITE DE LILLE 2 DROIT ET SANTE, Lille (FR)

(72) Inventors: Nicolas Sergeant, Lille (FR); Luc Buee, Lille (FR); Patricia Melnyk, Lille (FR); Marion Gay, Lille (FR); Nicolas Le Fur, Roubaix (FR)

(73) Assignees: INSERM (Institut National de la Sante et de la Recherche Medicale), Paris (FR); CENTRE HOSPITALIER REGIONAL ET UNIVERSITAIRE DE LILLE (CHRU), Lille (FR); UNIVERSITE DE LILLE 2 DROIT ET SANTE, Lille (FR)

(*) Notice: Subject to any disclaimer, the term of this patent is extended or adjusted under 35 U.S.C. 154(b) by 0 days.

(21) Appl. No.: 15/558,921

(22) PCT Filed: Mar. 16, 2016

(86) PCT No.: PCT/EP2016/055633
§ 371 (c)(1),
(2) Date: Sep. 15, 2017

(87) PCT Pub. No.: WO2016/146655
PCT Pub. Date: Sep. 22, 2016

(65) Prior Publication Data
US 2018/0072679 A1 Mar. 15, 2018

(30) Foreign Application Priority Data
Mar. 16, 2015 (EP) ...................................... 15305384

(51) Int. Cl.
*C07D 219/12* (2006.01)
(52) U.S. Cl.
CPC ................................. *C07D 219/12* (2013.01)
(58) Field of Classification Search
CPC .................................................. C07D 219/12
USPC .......................................................... 544/361
See application file for complete search history.

(56) References Cited

U.S. PATENT DOCUMENTS

2009/0149464 A1 6/2009 Sergeant et al.

FOREIGN PATENT DOCUMENTS

WO 2006/051489 A1 5/2006
WO 2014/028777 A2 2/2014
WO 2014102339 A1 7/2014

OTHER PUBLICATIONS

Danel, Journal of Chromatography A, 1455 (2016) 163-171.*
Belarbi, K. et al. "Loss of medial septum cholinergic neurons in THY-Tau22 mouse model: what links with tau pathology?" Current Alzheimer Research (2011) vol. 8(6), pp. 633-638.
Bretteville, A. et al. "Two-dimensional electrophoresis of tau mutants reveals specific phosphorylation pattern likely linked to early tau conformational changes" PLoS One (2009) vol. 4(3), pp. e4843.
Fernandez-Gomez, FJ et al."Consensus brain-derived protein, extraction protocol for the study of human and murine brain proteome using both 2D-DIGE and mini 2DE immunoblotting" Journal of Visualized Experiments( 2014) vol. 86 e51339 pp. 1-8.
Laurent, C. et al. "A2A adenosine receptor deletion is protective in a mouse model of Tauopathy" Molecular Psychiatry (2014) vol. 21, pp. 97-107.
Le Freche, H. et al. "Tau phosphorylation and sevoflurane anesthesia: an association to postoperative cognitive impairment" Anesthesiology (2012) vol. 116(4), pp. 779-787.
Maurage, C-A. et al. "Phosphorylated serine 199 of microtubule-associated protein tau is a neuronal epitope abundantly expressed in youth and an early marker of tau pathology" Acta Neuropathol (2003) vol. 105(2), pp. 89-97.
Ryckebusch, A. et al. "Synthesis and in Vitro and in Vivo Antimalarial Activity of N1-(7-Chloro-4-quinolyl)-1,4-bis(3-aminopropyl)piperazine Derivatives" Journal of Medicinal Chemistry (2003) vol. 46, pp. 542-557.
Sergeant, N. et al. "Neurofibrillary degeneration in progressive supranuclear palsy and corticobasal degeneration: tau pathologies with exclusively "exon 10" isoforms" Journal of Neurochemistry (1999) vol. 72(3), pp. 1243-1249.
Troquier, L. et al. "Targeting phospho-Ser422 by active Tau Immunotherapy in the THYTau22 mouse model: a suitable therapeutic approach" Curr Alzheimer Res. (2012) vol. 9(4), pp. 397-405.
Van der Jeugd, A. et al. "Progressive age-related cognitive decline in tau mice" Journal of Alzheimer's Disease (2103) vol. 37(4), pp. 777-788.

(Continued)

*Primary Examiner* — Nizal S Chandrakumar
(74) *Attorney, Agent, or Firm* — McDonnell Boehnen Hulbert & Berghoff LLP

(57) ABSTRACT

The present invention relates to the compound having Formula (I) or pharmaceutically acceptable salts or solvates thereof, and its use in treating and/or preventing a Tauopathy.

(I)

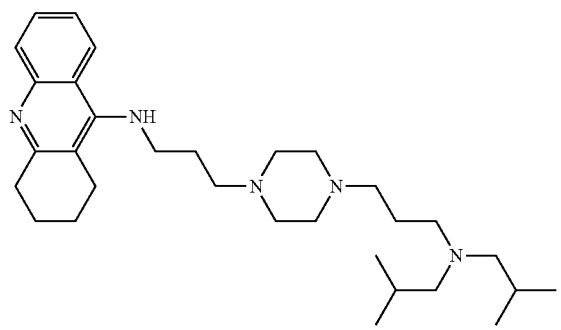

2 Claims, 6 Drawing Sheets

(56) References Cited

OTHER PUBLICATIONS

Melnyk, Patricia et al. "Chloroquine and chloroquinoline derivatives as models for the design of modulators of amyloid peptide precursor metabolism" ASC Chemical Neuroscience (2015) vol. 6, pp. 559-569.

The International Search Report (ISR) for PCT/EP2016/055633 dated Apr. 19, 2016, pp. 1-4.

The Written Opinion of the International Searching Authority for PCT/EP2016/055633 dated Apr. 19, 2016, pp. 1-5.

* cited by examiner

1,4-BIS(3-AMINOPROPYL)PIPERAZINE DERIVATIVE AND ITS USE

This application is a U.S. national phase of International Application No. PCT/EP2016/055633, filed Mar. 16, 2016, which claims priority from European Patent application no. EP 15305384, filed Mar. 16, 2015, the disclosure of each of which is hereby incorporated by reference in its entirety.

The present invention relates to a novel compound, N-[3-(4-{3-[Bis(2-methylpropyl)amino]propyl}piperazin-1-yl)propyl]-1,2,3,4-tetrahydroacridin-9-amine, and pharmaceutically acceptable salts or solvates thereof, their preparation, pharmaceutical compositions containing them and use of the same in the treatment and/or prevention of Tauopathies.

BACKGROUND OF THE INVENTION

N-[3-(4-{3-[Bis(2-methylpropyl)amino]propyl}piperazin-1-yl)propyl]-1,2,3,4-tetrahydroacridin-9-amine which has the structure of Formula I:

Formula I

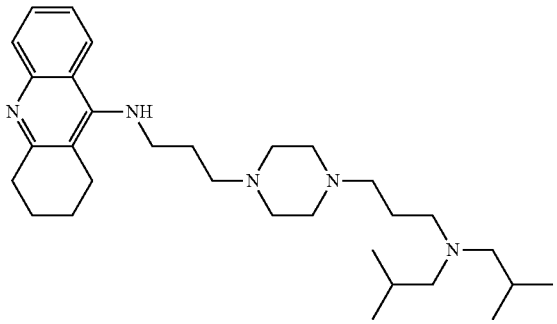

belongs to a family of 1,4-bis(3-aminopropyl)piperazine derivatives previously disclosed in WO 2006/051489 and which are useful for the treatment and/or prevention of neurodegenerative diseases with APP dysfunction.

A majority of neurodegenerative diseases have common cellular and molecular mechanisms including protein aggregation and inclusion body formation.

The definition of the different types of lesions is made regarding the molecular compound which constitutes them. Neurofibrillary degeneration (NFD) is one of the most widely observed brain lesions which results from a cascade of molecular events combining abnormal modifications of the microtubule-associated Tau protein isoforms, their progressive aggregation and accumulation into fibrillar material inside neurons.

Tau protein is mainly expressed in neurons of the central nervous system where it interacts with tubulin to stabilize microtubules and promotes tubulin assembly into microtubules. This stabilizing property is controlled by isoforms and phosphorylation. The Tau isoforms are the product of alternative splicing from transcript of a single gene MAPT (microtubule-associated protein Tau) located on chromosome 17.

Six Tau isoforms exist in human brain tissue, and they are distinguished by their number of binding domains (three or four binding domains). The isoforms are a result of alternative splicing in exons 2, 3, and 10 of the Tau gene. The binding domains are located in the half carboxy-terminal region of the protein and are positively-charged (allowing it to bind to the negatively-charged microtubule). The isoforms with four binding domains containing exon 10 have a better affinity with microtubules, thus allowing a better stabilization of these microtubules, than those with three binding domains.

Tau is a phosphoprotein, the phosphorylation sites of which are essentially distributed on both sides of the microtubule binding domain. The phosphorylation of Tau results in disruption of microtubule organization.

In several neurodegenerative diseases termed "Tauopathies", abnormally and hyperphosphorylated Tau protein isoforms aggregate into fibrillar structures within neurons to form the so-called neurofibrillary tangles (NFTs). These Tauopathies mainly differ from each other in both Tau isoform phosphorylation and content. Hyperphosphorylation, abnormal phosphorylation and aggregation are constantly present in neurofibrillary degeneration.

The quality, intensity and/or spatial location of neurofibrillary degeneration is extremely correlated with the impairment of cognitive functions. These impairments are particularly incapacitating for the patient who is not autonomous any more.

As a consequence, there is a need for treatments able to avoid the pathological aggregation of Tau protein in the human brain and the consequences of this aggregation.

Some treatments have focused on kinase inhibitors, phosphatase activators or anti-Tau antibodies (see for example WO 2014028777). However, none of these treatments have successfully led to a commercial treatment of Tauopathies up to the Applicant's knowledge, especially in the case of rare neurodegenerative diseases such as Pick's disease, Progressive supranuclear palsy (PSP), Corticobasal degeneration or Frontotemporal dementia with Parkinsonism linked to chromosome 17 (FTDP-17) mutations of MAPT.

There is thus still a need in the art for a treatment for Tauopathies able to successfully reestablish a normal Tau metabolism.

SUMMARY OF THE INVENTION

The present invention is based on the unexpected findings that the compound of Formula I, N-[3-(4-{3-[Bis(2-methylpropyl)amino]propyl}piperazin-1-yl)propyl]-1,2,3,4-tetrahydroacridin-9-amine, is useful in rectifying the metabolism of the Tau protein in particular by altering pathological Tau protein phosphorylation and by increasing Tau protein proteolysis.

The invention is thus directed to the compound of Formula I or pharmaceutically acceptable salts or solvates thereof, as well as compositions comprising such compounds and their use in treating and/or preventing a Tauopathy.

DETAILED DESCRIPTION OF THE INVENTION

The invention concerns the compound having Formula I

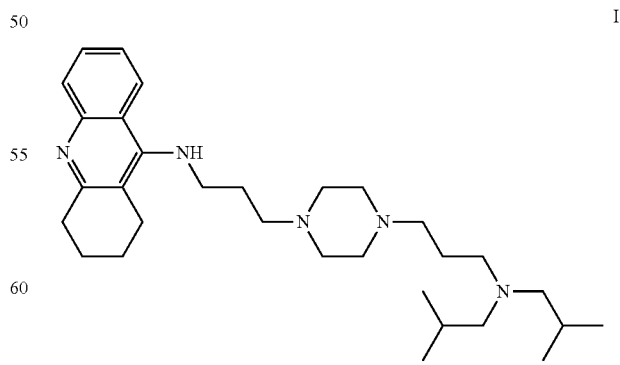

or pharmaceutically acceptable salts or solvates thereof.

The compound of Formula I as well as its pharmaceutically acceptable salts or solvates may be isotopically labelled, especially deuterated. The deuterated form is useful for the dosage of the compound in a biological environment.

The compound of formula I or pharmaceutically acceptable salts or solvates thereof are useful for rectifying the metabolism of the Tau protein on the following essential points:
1) decreasing the phosphorylation of Tau protein;
2) increasing the catabolite products of Tau protein.

By "Tauopathy" is meant a disorder characterized by an abnormal metabolism of Tau protein, in particular by an abnormal phosphorylation and/or hyperphosphorylation of Tau protein and/or the presence of elevated (higher than a normal control level, e.g. higher than a normal, control level for an individual or population of individuals of the same age group) levels of Tau or Tau isoform or Tau polypeptides and/or pathological forms of Tau in a cell, a tissue, or a fluid, preferably in brain tissue and/or cerebrospinal fluid. More specifically, a Tauopathy refers to a disorder wherein intracellular aggregates of abnormally modified Tau proteins are observed such as neurofibrillary tangles (NFT), Pick bodies, astrocytic tufted and/or muscle inclusion bodies, preferably at least neurofibrillary tangles (NFT).

Tauopathies include, but are not limited to, Alzheimer's disease, Amyotrophic lateral sclerosis and parkinsonism-dementia complex of Guam, Argyrophilic grain disease, Chronic traumatic encephalopathy, cerebral amyloid angiopathy, Corticobasal degeneration, Creutzfeldt-Jakob disease, Dementia pugilistica, Diffuse neurofibrillary tangles with calcification, Down's syndrome, Familial British Dementia, Familial Danish Dementia, Frontotemporal dementia (FTD), Frontotemporal dementia with Parkinsonism linked to chromosome 17 (FTDP-17), Gerstmann-Sträussler-Scheinker disease, Guadeloupean parkinsonism, Hallervorden-Spatz disease, inclusion body myositis, multiple system atrophy, Steinert Myotonic dystrophy, Myotonic dystrophy type II, Huntington disease Neurodegeneration with brain iron accumulation, Niemann-Pick disease of type C, Non-Guamanian motor neuron disease with neurofibrillary tangles, Paget's disease, Pick's disease, Postencephalitic parkinsonism, Prion protein cerebral amyloid angiopathy, Progressive subcortical gliosis, Progressive supranuclear palsy (PSP), SLC9A6-related mental retardation, Subacute sclerosing panencephalitis, Tangle-only dementia, multi-infarct dementia, ischemic stroke, chronic traumatic encephalopathy (CTE), traumatic brain injury (TBI), stroke and White matter Tauopathy with globular glial inclusions.

Due to its ability to rectify the metabolism of Tau protein as described above, the compound of Formula I or a pharmaceutically salt or solvate thereof is useful as a medicament, in particular for use in treating or preventing a Tauopathy.

Hence, the invention also concerns the compound of Formula I or a pharmaceutically acceptable salt or solvate thereof as defined herein for use in treating and/or preventing a Tauopathy selected from Alzheimer's disease, Amyotrophic lateral sclerosis and parkinsonism-dementia complex, Argyrophilic grain disease, Chronic traumatic encephalopathy, cerebral amyloid angiopathy, Corticobasal degeneration, Creutzfeldt-Jakob disease, Dementia pugilistica, Diffuse neurofibrillary tangles with calcification, Down's syndrome, Familial British Dementia, Familial Danish Dementia, Frontotemporal dementia (FTD), Frontotemporal dementia with Parkinsonism linked to chromosome 17 (FTDP-17), Frontotemporal lobar degeneration, Gerstmann-Sträussler-Scheinker disease, Guadeloupean parkinsonism, Hallervorden-Spatz disease, inclusion body myositis, multiple system atrophy, Myotonic dystrophy, Neurodegeneration with brain iron accumulation, Niemann-Pick disease, Non-Guamanian motor neuron disease with neurofibrillary tangles, Pick's disease, Postencephalitic parkinsonism, Prion protein cerebral amyloid angiopathy, Progressive subcortical gliosis, Progressive supranuclear palsy (PSP), SLC9A6-related mental retardation, Subacute sclerosing panencephalitis, Tangle-only dementia, multi-infarct dementia, ischemic stroke, chronic traumatic encephalopathy (CTE), traumatic brain injury (TBI), stroke and White matter Tauopathy with globular glial inclusions. More preferably, the Tauopathy is selected from Alzheimer's disease, Frontotemporal dementia with Parkinsonism linked to chromosome 17 (FTDP-17), Progressive supranuclear palsy (PSP), Corticobasal degeneration, Pick's disease and Frontotemporal Dementia (FTD). More preferably, the Tauopathy is selected from Frontotemporal dementia with Parkinsonism linked to chromosome 17 (FTDP-17), Progressive supranuclear palsy (PSP), Corticobasal degeneration, Pick's disease and Frontotemporal Dementia (FTD).

In other terms, the invention also provides for a method of treating and/or preventing a Tauopathy, in particular those cited above as well as embodiments thereof, comprising administering to a patient in need thereof a pharmaceutically effective amount of the compound of Formula I or a pharmaceutically acceptable salt or solvate thereof as described herein.

In one particular embodiment, the invention also concerns a compound of Formula I or a pharmaceutically acceptable salt or solvate thereof as defined herein for use in delaying in a patient the onset of a Tauopathy as described above.

In other terms, the invention provides a method for delaying in a patient the onset of a Tauopathy, comprising administering to a patient in need thereof a pharmaceutically effective amount of the compound of Formula I or a pharmaceutically acceptable salt or solvate thereof.

According to a further feature of the present invention there is provided a method for modulating pathological Tau metabolism, in a patient, preferably a warm blooded animal, and even more preferably a human, in need of such treatment, which comprises administering to said patient an effective amount of the compound of Formula I, or a pharmaceutically acceptable salt or solvate thereof.

More preferably, there is provided a method for altering pathological Tau protein phosphorylation in a patient, preferably a warm blooded animal, and even more preferably a human, in need of such treatment, which comprises administering to said patient an effective amount of the compound of Formula I or a pharmaceutically acceptable salt or solvate thereof.

Generally, for pharmaceutical use, the compound of Formula I or a pharmaceutically acceptable salt or solvate thereof may be formulated as a pharmaceutical composition comprising at least the compound of the invention or a pharmaceutically acceptable salt or solvate thereof and at least one pharmaceutically acceptable carrier, diluent, excipient and/or adjuvant, and optionally one or more additional therapeutic agents and/or active ingredients.

By means of non-limiting examples, the pharmaceutical composition may be in a dosage form suitable for oral administration, for parenteral administration (such as by intravenous, intramuscular or subcutaneous injection or intravenous infusion), for topical administration (including ocular), for administration by inhalation, by a skin patch, by an implant, by a suppository, etc. Such suitable administration forms—which may be solid, semi-solid or liquid, depending on the manner of administration—as well as methods and carriers, diluents and excipients for use in the preparation thereof, will be clear to the skilled person; reference is made to the latest edition of Remington's Pharmaceutical Sciences. The pharmaceutical compositions may be formulated in solid form and re-dissolved or suspended prior to use.

Some preferred, but non-limiting examples of dosage forms include tablets, pills, powders, lozenges, sachets, cachets, elixirs, suspensions, emulsions, solutions, syrups, aerosols, ointments, cremes, lotions, soft and hard gelatin capsules, suppositories, drops, sterile injectable solutions and sterile packaged powders (which are usually reconstituted prior to use) for administration as a bolus and/or for continuous administration, which may be formulated with carriers, excipients, and diluents that are suitable per se for such formulations, such as lactose, dextrose, sucrose, sorbitol, mannitol, starches, gum acacia, calcium phosphate, alginates, tragacanth, gelatin, calcium silicate, microcrystalline cellulose, polyvinylpyrrolidone, polyethylene glycol, cellulose, (sterile) water, methylcellulose, methyl- and propylhydroxybenzoates, talc, magnesium stearate, edible oils, vegetable oils and mineral oils or suitable mixtures thereof. The pharmaceutical compositions can optionally contain other substances that are commonly used in pharmaceutical formulations, such as lubricating agents, wetting agents, emulsifying and suspending agents, dispersing agents, disintegrating agents, stabilizing agents, isotonic agents, bulking agents, fillers, preserving agents, sweetening agents, flavoring agents, perfuming agents, coloring agents, antibacterial agents and/or antifungal agents such as parabens, chlorobutanol, phenol, sorbic acid, dispensing agents, flow regulators, release agents, etc. The compositions may also be formulated so as to provide rapid, sustained or delayed release of the active compound(s) contained therein.

The pharmaceutical compositions of the invention are preferably in a unit dosage form, and may be suitably packaged, for example in a box, blister, vial, bottle, sachet, ampoule or in any other suitable single-dose or multi-dose holder or container (which may be properly labeled); optionally with one or more leaflets containing product information and/or instructions for use. Generally, such unit dosages will contain between 0.05 and 1000 mg, and usually between 1 and 500 mg, of the at least one compound of the invention, e.g. about 10, 25, 50, 100, 200, 300 or 400 mg per unit dosage.

Usually, depending on the condition to be prevented or treated and the route of administration, the active compound of the invention will usually be administered between 0.01 to 100 mg per kilogram, more often between 0.1 and 50 mg, such as between 1 and 25 mg, for example about 0.5, 1, 5, 10, 15, 20 or 25 mg, per kilogram body weight of the patient per day, which may be administered as a single daily dose, divided over one or more daily doses, or essentially continuously, e.g. using a drip infusion.

The compound of Formula I of the invention and its pharmaceutically acceptable salts and solvates can be prepared by different ways with reactions known by the person skilled in the art. Reaction schemes as described in the example section illustrate by way of example different possible approaches.

The salts and solvates thereof can be prepared according to techniques known in the art such as those involving precipitation, crystallization, recrystallization, lyophilisation, phase transfer or ion exchange resins.

Generally, pharmaceutically acceptable salts of compounds of Formula I may for example be prepared as follows:

(i) by reacting the compound of Formula I with the desired acid;

(ii) by converting one salt of the compound of Formula I to another by reaction with an appropriate acid or by means of a suitable ion exchange column.

All these reactions are typically carried out in solution. The salt, may precipitate from solution and be collected by filtration or may be recovered by evaporation of the solvent. The degree of ionization in the salt may vary from completely ionized to almost non-ionized.

Definitions

The definitions and explanations below are for the terms as used throughout the entire application, including both the specification and the claims.

Unless otherwise stated any reference to compounds of the invention herein, means the compound of Formula I as such as well as their pharmaceutically acceptable salts and/or solvates.

When describing the compounds of the invention, the terms used are to be construed in accordance with the following definitions, unless indicated otherwise.

The terms "salt" refers to any acid addition salt obtained from the compound of the invention, said salt having an essentially similar biological activity compared to the biological activity of the compound of the invention. Suitable pharmaceutically acceptable acid addition salts are formed from acids which form non-toxic salts. Non-limiting examples include the acetate, adipate, aspartate, benzoate, besylate, bicarbonate, carbonate, bisulphate, sulphate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinofoate salts. Hemisalts of acids may also be formed, for example, hemisulphate salts. Preferably, pharmaceutically acceptable salts include the hydrochloride, hydrobromide, bisulphate, sulphate, nitrate, citrate, acetate, and phosphate salts. The hydrochloride is particularly preferred.

The term "solvate" is used herein to describe a molecular complex comprising the compound of the invention and one or more pharmaceutically acceptable solvent molecules, for example, ethanol or water. The term "hydrate" is employed when said solvent is water.

All references to compounds of Formula I include references to pharmaceutically acceptable salts and solvates thereof.

The compounds of the invention include compounds of Formula I as hereinbefore defined, including all polymorphs and crystal habits thereof, prodrugs and isomers thereof (including optical, geometric and tautomeric isomers) and isotopically labeled compounds of Formula I.

The term "patient" refers to a warm-blooded animal, more preferably a human, who/which is awaiting the receipt of, or is receiving medical care or is/will be the object of a medical procedure.

The term "human" refers to a subject of both genders and at any stage of development (i.e. neonate, infant, juvenile, adolescent, adult). In one embodiment, the human is an adolescent or adult, preferably an adult.

The terms "treat", "treating" and "treatment, as used herein, are meant to include alleviating, attenuating or abrogating a condition or disease and/or its attendant symptoms.

The terms "prevent", "preventing" and "prevention", as used herein, refer to a method of delaying or precluding the onset of a condition or disease and/or its attendant symptoms, barring a patient from acquiring a condition or disease, or reducing a patient's risk of acquiring a condition or disease.

The term "therapeutically effective amount" (or more simply an "effective amount") as used herein means the amount of active agent or active ingredient (e.g. N-[3-(4-{3-[Bis(2-methylpropyl)amino]propyl}piperazin-1-yl)propyl]-1,2,3,4-tetrahydroacridin-9-amine) that is sufficient to achieve the desired therapeutic or prophylactic effect in the patient to which/whom it is administered.

The term "administration", or a variant thereof (e.g., "administering"), means providing the active agent or active ingredient (e.g. N-[3-(4-{3-[Bis(2-methylpropyl)amino]propyl}piperazin-1-yl)propyl]-1,2,3,4-tetrahydroacridin-9-amine), alone or as part of a pharmaceutically acceptable composition, to the patient in whom/which the condition, symptom, or disease is to be treated or prevented.

By "pharmaceutically acceptable" is meant that the ingredients of a pharmaceutical composition are compatible with each other and not deleterious to the patient thereof.

The term "pharmaceutical vehicle" as used herein means a carrier or inert medium used as solvent or diluent in which the pharmaceutically active agent is formulated and/or administered. Non-limiting examples of pharmaceutical vehicles include creams, gels, lotions, solutions, and liposomes.

The present invention will be better understood with reference to the following examples. These examples are intended to representative of specific embodiments of the invention, and are not intended as limiting the scope of the invention.

A: Representation of the distance to reach the platform (path length) in function of time (days).

B: Representation of the percent of time spent in the target quadrant ("T") (where the platform is positioned during the learning phase) versus the others ("O").

Figure 5:
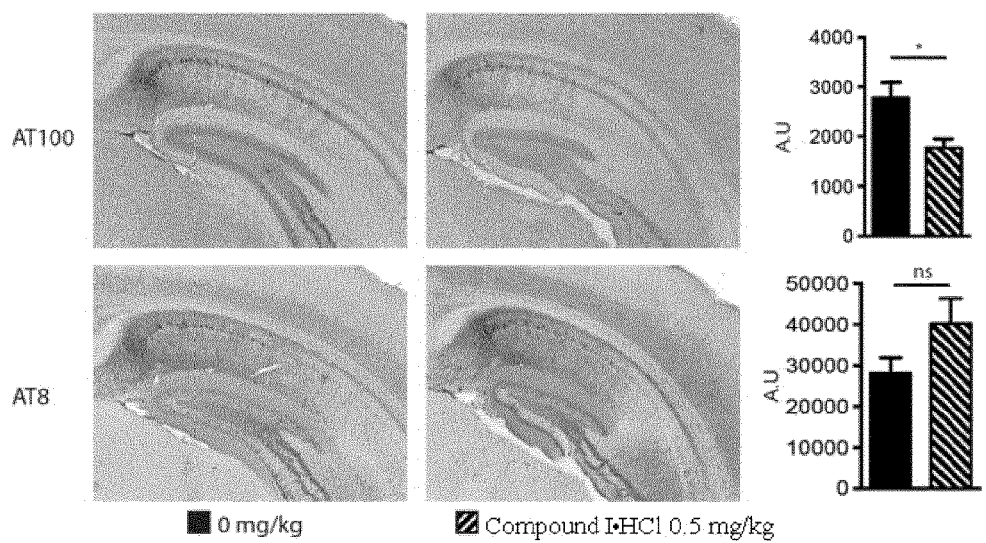

FIG. 5: Immunohistochemical measurement of tau pathology in Thy-Tau22 mice untreated (0 mg/kg) or treated with Compound I.HCl (0.5 mg/kg Compound I.HCl).

Figure 6:
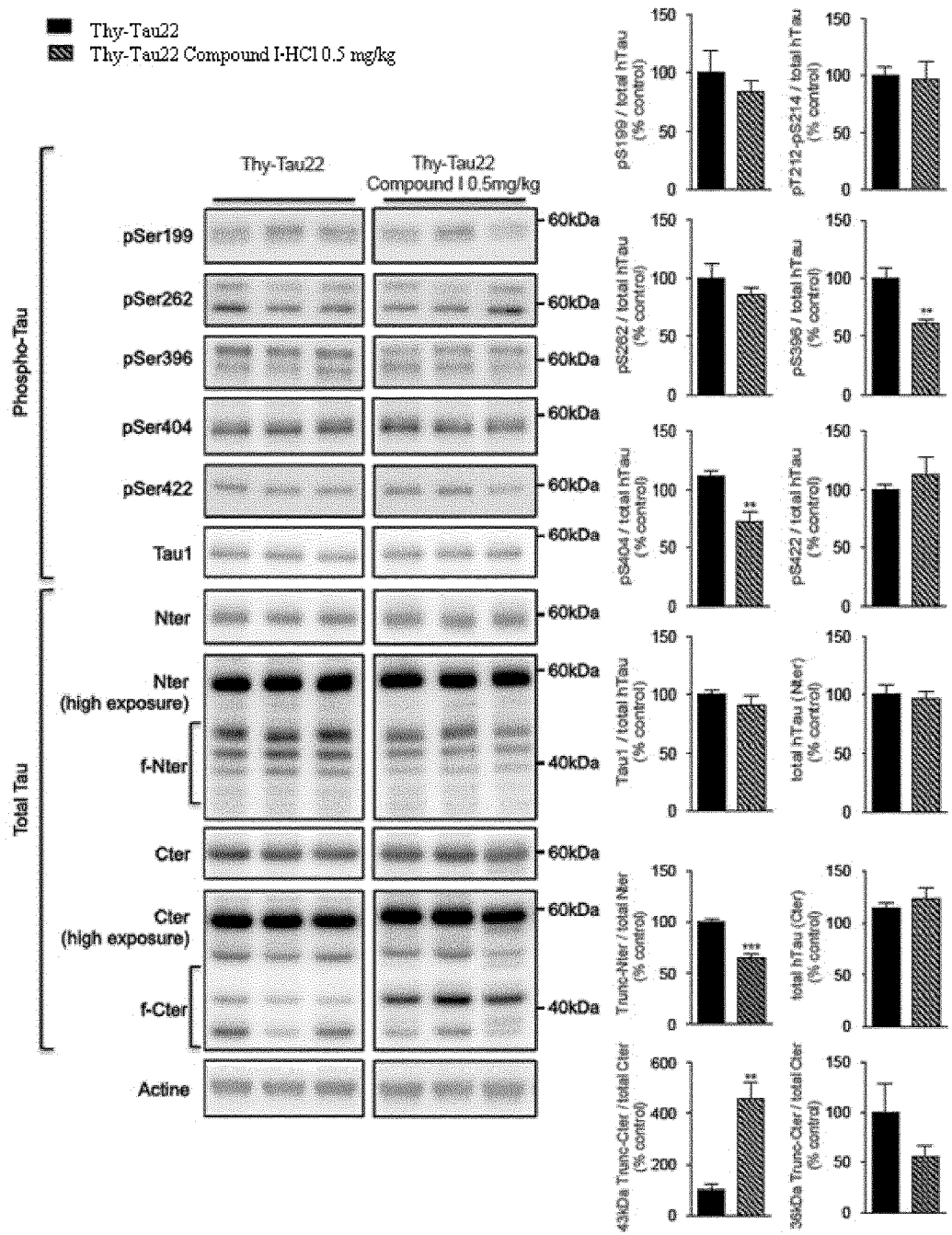

FIG. 6: Biochemical analysis of Tau expression, catabolites and phosphorylation by 1D SDS-PAGE and Western-blot.

CHEMISTRY EXAMPLES

The following abbreviations are used throughout the present application: ° C.: Celsius degrees, BINAP: 2,2'-bis (diphenylphosphino)-1,1'-binaphtyl, dba: dibenzylideneacetone, DCE: dichloroethane, DCM: dichloromethane, δ: NMR chemical shifts expressed in ppm, eq: equivalent(s), Et: ethyl, g: gram(s), HPLC: high performance liquid chromatography, L: liter(s), LCMS: HPLC coupled to a mass spectrometer, Me: methyl, mg: milligram(s), min: minute(s), mL: milliliter(s), mol: mole(s), mmol: millimole(s), μmol: micromole(s), MS: Mass Spectrometry, NMR: nuclear magnetic resonance, ppm: party per million, RT: room temperature (ca 15-25° C.), Xantphos: 4,5-Bis(diphenylphosphino)-9,9-dimethylxanthene, rt: retention time.

All reported temperatures are expressed in degrees Celsius (° C.); all reactions were carried out at room temperature (RT) unless otherwise stated.

Material and Methods

Chemicals and solvents were obtained from commercial sources, and used without further purification unless otherwise precised. Reactions were monitored by TLC performed on Macherey-Nagel Alugram® Sil 60/UV$_{254}$ sheets (thickness 0.2 mm). Purification of products was carried out by either column chromatography using Macherey-Nagel silica gel (230-400 mesh).

NMR spectra were recorded on a Bruker DRX 300 spectrometer (operating at 300 MHz for $^1$H and 75 MHz for $^{13}$C). Chemical shifts are expressed in ppm relative to either tetramethylsilane (TMS) or to residual proton signal in deuterated solvents. Chemical shifts are reported as position (δ in ppm), multiplicity (s=singlet, d=doublet, t=triplet, sept=septuplet, br=broad and m=massif), coupling constant (J in Hz), relative integral and assignment. The attributions of protons and carbons were achieved by analysis of 1D and 2D experiments ($^1$H, $^{13}$C).

Mass spectra were recorded on a Varian triple quadrupole 1200 W mass spectrometer equipped with a non-polar C18 TSK-gel Super ODS (4.6×50 mm) column, using electrospray ionization and a UV detector (diode array).

The compound of formula I can be prepared according to the three methods set out in Scheme 1 below.

Scheme 1

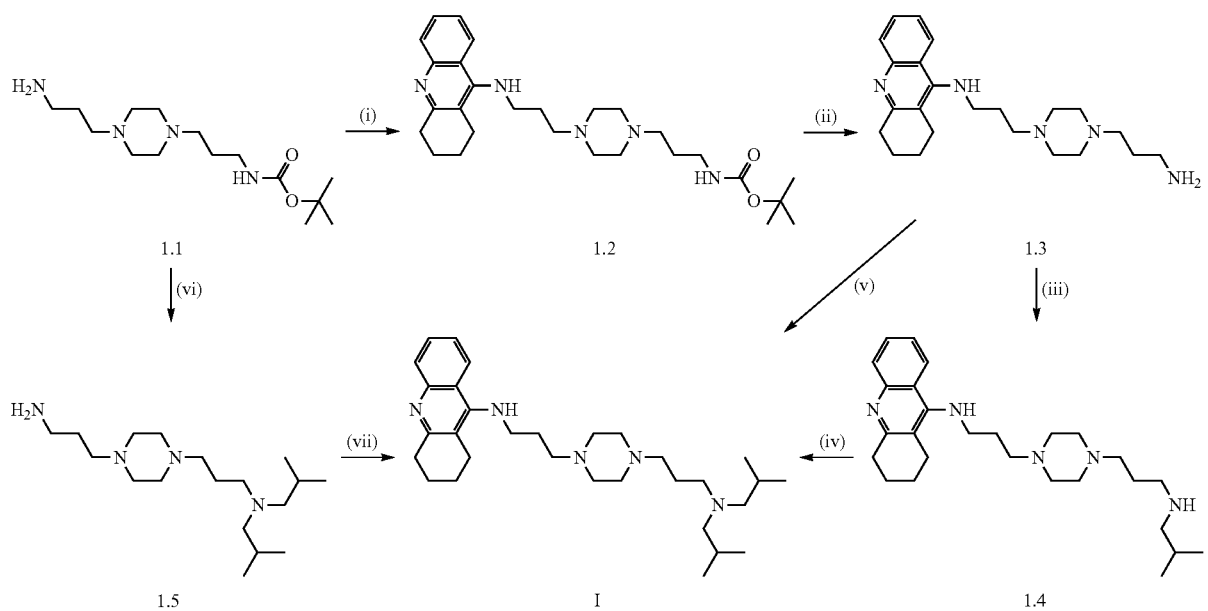

Reagents and conditions: (i) 9-Chloro-1,2,3,4-tetrahydroacridine, Cs$_2$CO$_3$, Xantphos, Pd$_2$(dba)$_3$, dioxane, reflux; (ii) Dioxane saturated in HCl, 20° C.; (iii) Isobutyraldehyde, NaBH$_4$, DCE, 20° C.; (iv) Isobutyraldehyde or Isobutyraldehyde-d$_7$, NaBH$_4$, DCE, 20° C.; (v) Isobutyraldehyde or Isobutyraldehyde-d$_7$, STAB, DCM, 20° C. (vi) J. Med. Chem. 2003, 46, 542-557; (vii) 9-Chloro-1,2,3,4-tetrahydroacridine, Cs$_2$CO$_3$, BINAP, Pd$_2$(dba)$_3$, dioxane, reflux.

EXAMPLE 1

Synthesis of tert-Butyl N-[3-(4-{3-[(1,2,3,4-tetrahydroacridin-9-yl)amino]propyl}piperazin-1-yl)propyl]carbamate (1.2)

To an oven-dried flask and under nitrogen atmosphere, were placed 9-chloro-1,2,3,4-tetrahydroacridine (0.50 g, 2.3 mmol), Cs$_2$CO$_3$ (1.05 g, 3.22 mmol) in dioxane (7.45 mL). The mixture was deoxygenated by passing a stream of nitrogen through it. Xantphos (0.20 g, 0.35 mmol) and Pd$_2$(dba)$_3$ (0.11 g, 0.12 mmol) were added. Then tert-butyl N-{3-[4-(3-aminopropyl)piperazin-1-yl]propyl}carbamate 1.1 prepared according to J. Med. Chem. 2003, 46, 542-557 (0.83 mg, 2.76 mmol) dissolved in dioxane (7.45 mL) was added to the mixture. The reaction mixture was stirred for 24 hours. The solution was filtered through a celite pad and evaporated. The residue was purified by flash chromatography (eluent DCM/MeOH 0 to 10% then DCM/MeOH sat NH3 0 to 4%. The title compound (1.00 g, 90% yield) was obtained as yellow oil.

$^1$H NMR (300 MHz), δ (ppm, CDCl$_3$): 7.95 (dd, $^3$J=1.1 Hz, $^3$J=8.5 Hz, 1H); 7.82 (dd, $^3$J=0.9 Hz, $^3$J=8.6 Hz, 1H); 7.45 (ddd, $^4$J=1.2 Hz, $^3$J=6.8 Hz, $^3$J=8.2 Hz, 1H); 7.24 (ddd, $^4$J=1.2 Hz, $^3$J=6.8 Hz, $^3$J=8.3 Hz, 1H); 5.53 (br t, $^3$J=5.2 Hz, 1H); 5.06 (br t, $^3$J=5.4 Hz, 1H); 3.48 (m, 2H); 3.12 (m, 2H); 2.98 (t, $^3$J=6.0 Hz, 2H); 2.66 (t, $^3$J=6.0 Hz, 2H); 2.55-2.32 (M, 12H); 1.85-1.72 (M, 6H); 1.59 (m, 2H), 1.35 (s, 9H).

$^{13}$C NMR (75 MHz), δ (ppm, CDCl$_3$): 158.4; 156.0; 151.0; 147.5; 128.7; 128.0; 123.3; 123.0; 120.3; 115.9; 78.7; 57.0; 53.2; 48.9; 39.8; 34.0; 28.4; 27.2; 26.4; 25.7; 22.9.

LC-MS (ESI) m/z Calculated: 482.3, Found: 482.4 [M+H]$^+$, 382.2 [M+H-Boc]$^+$; rt: 1.8 min.

EXAMPLE 2

N-{3-[4-(3-Aminopropyl)piperazin-1-yl]propyl}-1,2,3,4-tetrahydroacridin-9-amine (1.3)

tert-Butyl N-[3-(4-{3-[(1,2,3,4-tetrahydroacridin-9-yl)amino]propyl}piperazin-1-yl)propyl]carbamate 1.2 (90 mg, 0.19 mmol) was dissolved in dioxane saturated with HCl (5 mL). The reaction mixture was stirred for 15 hours. The solvent was evaporated. The residue was dissolved in MeOH (NH$_3$) and stirred for 2 hours. The solvent was evaporated. The residue was dissolved in 15 mL of DCM and washed with saturated NaHCO$_3$ solution (3×10 mL). The organic layer was dried over MgSO$_4$, filtered and evaporated. The residue was purified by column chromatography (eluent DCM/MeOH(NH$_3$) 9.4:0.6 (v/v)). The title compound (70 mg, 98% yield) was obtained as yellow oil.

$^1$H NMR (300 MHz), δ (ppm, CDCl$_3$): 8.01 (dd, $^4$J=0.9 Hz, $^3$J=8.5 Hz, 1H); 7.87 (dd, $^4$J=0.9 Hz, $^3$J=8.5 Hz, 1H); 7.51 (ddd, $^4$J=1.4 Hz, $^3$J=6.8 Hz, $^3$J=8.3 Hz, 1H); 7.30 (ddd, $^4$J=1.3 Hz, $^3$J=6.8 Hz, $^3$J=8.3 Hz, 1H); 5.13 (br s, 1H); 3.55 (t, $^3$J=6.0 Hz, 2H); 3.04 (t, $^3$J=6.4 Hz, 2H); 2.71 (M, 4H); 2.65-2.37 (M, 12H); 1.91-1.79 (M, 8H); 1.64 (m, 2H).

$^{13}$C NMR (75 MHz), δ (ppm, CDCl$_3$): 158.4; 151.1; 147.5; 128.7; 128.1; 123.4; 123.0; 120.3; 115.9; 57.0; 53.4; 49.0; 40.8; 34.0; 30.5; 27.2; 25.7; 22.9.

LC-MS (ESI) m/z Calculated: 382.3, Found: 382.2 [M+H]$^+$; rt: 1.3 min.

EXAMPLE 3

N-[3-(4-{3-[(2-Methylpropyl)amino]propyl}piperazin-1-yl)propyl]-1,2,3,4-tetrahydroacridin-9-amine (1.4)

To a stirred solution of N-{3-[4-(3-aminopropyl)piperazin-1-yl]propyl}-1,2,3,4-tetrahydroacridin-9-amine 1.3 (100 mg, 0.26 mmol) in toluene (5 mL) was added isobutyraldehyde (0.04 mL, 0.4 mmol). The reaction mixture was refluxed with a Dean-Stark apparatus for 1 hour (until no more drops of water appeared). The toluene was evaporated and the residue was dissolved in DCE (5 mL). NaBH$_4$ (15 mg, 0.4 mmol) was added and the mixture was stirred for 15 hours. 10 mL of saturated NaHCO$_3$ solution was added. The mixture was stirred for 1 hour. 5 mL of DCM was added and the layers were separated. The organic layer was washed with saturated NaHCO$_3$ solution (2×10 mL). The organic layer was dried over MgSO$_4$, filtered and evaporated. The compound was used without purification for the next step.

$^1$H NMR (300 MHz), δ (ppm, CDCl$_3$): 8.03 (dd, $^4$J=1.0 Hz, $^3$J=8.5 Hz, 1H); 7.90 (dd, $^4$J=0.9 Hz, $^3$J=8.5 Hz, 1H); 7.54 (ddd, $^4$J=1.3 Hz, $^3$J=6.8 Hz, $^3$J=8.3 Hz, 1H); 7.33 (ddd, $^4$J=1.3 Hz, $^3$J=6.8 Hz, $^3$J=8.3 Hz, 1H); 5.14 (br s, 1H); 3.57 (m, 2H); 3.05 (t, $^3$J=6.2 Hz, 2H); 2.74 (t, $^3$J=5.5 Hz, 2H); 2.65 (t, $^3$J=6.9 Hz, 2H); 2.56-2.40 (M, 14H); 1.94-1.66 (M, 11H); 0.92 (d, $^3$J=6.6 Hz, 6H).

$^{13}$C NMR (75 MHz), δ (ppm, CDCl$_3$): 158.5; 151.1; 147.6; 128.8; 128.1; 123.4; 123.0; 120.3; 116.0; 58.2; 57.4; 53.5; 49.0; 34.1; 28.5; 27.2; 25.7; 23.0; 20.7.

LC-MS (ESI) m/z Calculated: 438.3, Found: 438.3 [M+H]$^+$; rt: 1.5 min.

EXAMPLE 4

Isobutyraldehyde-d7: 2-($^2$H$_3$)methyl(2,3,3,3-$^2$H$_4$) propanal

N-Methoxy-2-($^2$H$_3$)methyl-N-methyl($^2$H$_4$)propanamide

To a stirred solution of 2-($^2$H$_3$)methyl($^2$H$_4$)propanoic acid (93 μL, 1 mmol) in DCM (3.8 mL) was added N-methylmorpholine (0.715 mL, 6.5 mmol), EDC 1HCl (249 mg, 1.3 mmol), HOBt (175 mg, 1.3 mmol) and N,O-dimethylhydroxylamine hydrochloride (204 mg, 2.1 mmol). The mixture was stirred for 15 hours. 5 mL of DCM were added to the reaction mixture and the organic layer was washed with saturated NaHCO$_3$ solution (2×5 mL), HCl 1M solution (2×5 mL) and brine (1×5 mL).

The organic layer was used without evaporation or purification for the next step.

$^1$H NMR (300 MHz), δ (ppm, CDCl$_3$): 3.70 (s, 3H, H$_b$); 3.19 (s, 3H, H$_a$).

$^{13}$C NMR (75 MHz), δ (ppm, CDCl$_3$): 178.3; 61.4; 32.3; 29.1; 18.3.

LC-MS (ESI) m/z Calculated: 139.2, Found: 139.8 [M+H]$^+$

Isobutyraldehyde-d7: 2-($^2$H$_3$)methyl(2,3,3,3-$^2$H$_4$) propanal

To a solution of N-Methoxy-2-($^2$H$_3$)methyl-N-methyl ($^2$H$_4$)propanamide in DCM (5 mL, 1 mmol) was added LiAlH$_4$ (0.9 mL, 0.9 mmol). The mixture was stirred for 1 hour. Saturated KHSO$_4$ solution (4.2 mL) was added dropwise. 5 mL of DCM were added and the organic layer was washed with saturated NaHCO$_3$ solution (2×5 mL), HCl 1M solution (2×5 mL) and brine (1×5 mL). The organic layer was dried, filtered and used as it is.

EXAMPLE 5

N-[3-(4-{3-[Bis(2-methylpropyl)amino] propyl}piperazin-1-yl)propyl]-1,2,3,4-tetrahydroacridin-9-amine (I)

First Protocol (iv)

To a stirred solution of N-[3-(4-{3-[(2-methylpropyl) amino]propyl}piperazin-1-yl)propyl]-1,2,3,4-tetrahydroacridin-9-amine 1.4 (230 mg, 0.52 mmol) in toluene (10 mL) was added isobutyraldehyde (0.07 mL, 0.8 mmol). The reaction mixture was heated with a Dean-Stark apparatus for 1 hour (until no more drops of water appeared). The toluene was evaporated and the residue was dissolved in DCE (10 mL). NaBH$_4$ (30 mg, 0.8 mmol) was added and the mixture was stirred for 15 hours. 15 mL of saturated NaHCO$_3$ solution was added. The mixture was stirred for 1 hour. 10 mL of DCM was added and the layers were separated. The organic layer was washed with saturated NaHCO$_3$ solution (2×15 mL). The organic layer was dried over MgSO$_4$, filtrated and evaporated. The residue was purified by column chromatography on alumina (eluent DCM/MeOH(NH$_3$) 9.8: 0.2 (v/v)).

The title compound (30 mg, 12% yield) was obtained as colorless oil.

Second Protocol (v)

To the organic layer containing isobutyralehyde-d7 (Example 4) was added N-{3-[4-(3-aminopropyl)piperazin-1-yl]propyl}-1,2,3,4-tetrahydroacridin-9-amine 1.3 (80 mg, 0.21 mmol). The mixture was stirred for 1 hour and STAB (190 mg, 0.899 mmol) was added. The mixture was stirred for 15 hours. 5 mL of saturated NaHCO$_3$ solution was added and the mixture was stirred for 1 hour. The layers were separated and the organic layer was washed with saturated NaHCO$_3$ solution (2×5 mL). The organic layer was dried, filtrated and evaporated. The residue was purified by flash chromatography (DCM/MeOH(NH$_3$), 10:0 to 9.5:0.5 (v/v)).

The title compound (36 mg, 34% yield) was obtained as colorless oil.

Third Protocol (vii)

In a oven-dried flask and under a nitrogen atmosphere, were placed 9-chloro-1,2,3,4-tetrahydroacridine (257 mg, 1.12 mmol), (+/−) BINAP (167 mg, 0.15 eq), Cs$_2$CO$_3$ (546 mg, 1.4 eq), Pd$_2$(dba)$_3$ (162 mg, 0.15 eq) and 3 mL of dry 1,4-dioxane. N-[3-[4-(3-aminopropyl)piperazin-1-yl]propyl]-N-isobutyl-2-methyl-propan-1-amine 1.5 (349 mg, 2.07 mmol) prepared according to Ryckebusch A et al. J. Med. Chem. 2003, 46, 542-557 in dry dioxane (3 mL) was added and the mixture was stirred at 90° C. for 12 h. The solution was filtered through a celite pad and evaporated. The residue was purified by flash chromatography on silica gel (CH$_2$Cl$_2$/MeOH//95/5).

The title compound (419 mg, 12% yield) was obtained as colorless oil.

Characterization of N-[3-[4-(3-aminopropyl)piperazin-1-yl]propyl]-N-isobutyl-2-methyl-propan-1-amine 1.5

$^1$H NMR (300 MHz), δ (ppm, CD$_3$OD): 3.05 (t, $^3$J=7.2 Hz, 2H); 3.00-2.60 (M, 18H); 2.10-1.80 (M, 6H); 1.02 (d, $^3$J=6.5 Hz, 12H).

$^{13}$C NMR (75 MHz), δ (ppm, CD$_3$OD): 61.1; 53.8; 53.5; 50.7; 37.6; 24.2; 22.5; 21.3; 19.5.

LC-MS (ESI) m/z calculated: 313.3, found: 313.2 [M+H]$^+$; rt: 1.15 min.

Characterization of N-[3-(4-{3-[Bis(2-methylpropyl)amino]propyl}piperazin-1-yl)propyl]-1,2,3,4-tetrahydroacridin-9-amine I $^1$H-Compound $^1$H NMR (300 MHz), δ (ppm, CDCl$_3$): 8.45 (d, $^3$J=8.6 Hz, 1H); 7.8-7.9 (M, 2H); 7.64 (ddd, $^3$J=8.6 Hz, $^3$J=6.7 Hz, $^4$J=1.1 Hz, 1H); 4.14 (t, $^3$J=6.6 Hz, 2H); 3.6-4.1 (M, 8H); 3.35-3.55 (M, 6H); 3.11 (d, $^3$J=6.8 Hz, 4H); 3.0-3.1 (M, 2H); 2.79 (m, 2H); 2.5-2.3 (M, 4H); 2.20 (sept, $^3$J=6.6 Hz, 2H); 1.9-2.0 (M, 4H); 1.09 (d, $^3$J=6.5 Hz, 12H).

$^{13}$C NMR (75 MHz), δ (ppm, CDCl$_3$): 156.5; 150.9; 138.2; 132.8; 125.5; 124.9; 118.8; 115.9; 112.2; 61.1; 51.2; 44.3; 28.1; 24.7; 24.0; 21.6; 20.4; 19.5; 19.4; 18.1.

LC-MS (ESI) m/z Calculated: 494.4, Found: 494.4 [M+H]$^+$; rt: 1.4 min.

d14-Compound $^1$H NMR (300 MHz), δ (ppm, CDCl$_3$): 8.04 (dd, $^4$J=0.9 Hz, $^3$J=8.6 Hz, 1H, H$_5$); 7.90 (dd, $^4$J=0.7 Hz, $^3$J=7.7 Hz, 1H, H$_8$); 7.54 (ddd, $^4$J=1.3 Hz, $^3$J=6.8 Hz, $^3$J=8.2 Hz, 1H, H$_7$); 7.32 (ddd, $^4$J=1.2 Hz, $^3$J=6.8 Hz, $^3$J=8.3 Hz, 1H, H$_6$); 5.27 (br s, 1H, NH); 3.59 (m, 2H, H$_d$); 3.07 (t, $^3$J=5.4 Hz, 2H, H$_4$); 2.73 (t, $^3$J=5.8 Hz, 2H, H$_1$); 2.57-2.40 (M, 14H, H$_a$, H$_{a'}$, H$_b$, H$_{b'}$, H$_{d'}$); 2.04 (s, 4H, H$_e$); 1.96-1.82 (M, 6H, H$_2$, H$_3$, H$_{e'}$); 0.92 (m, 2H, H$_{e'}$).

$^{13}$C NMR (75 MHz), δ (ppm, CDCl$_3$): 158.3; 151.2; 147.3; 128.6; 128.2; 123.4; 123.1; 120.2; 115.8; 63.7; 57.4; 53.5; 49.2; 33.9; 27.2; 25.8; 22.9; 20.4; 19.4.

LC-MS (ESI) m/z Calculated: 508.5, Found: 508.4 [M+H]$^+$; rt: 1.5 min.

EXAMPLE 6

N-[3-(4-{3-[Bis(2-methylpropyl)amino]propyl}piperazin-1-yl)propyl]-1,2,3,4-tetrahydroacridin-9-amine hydrochloride The hydrochloride of the $^1$H compound of Example 5 obtained according to the third protocol of Example 5 was formed after treatment with MeOH/HCl. Compound of example 5 was solubilized in MeOH, treated with HCl 1M until pH=1 and then lyophilized.

BIOLOGICAL EXAMPLES

Materials and Methods

Antibodies

Pan-Tau and phospho-dependent Tau antibodies included Tau-Nter (M19G, 1/10 000, Sergeant et al., 1999), Tau-Cter (1/10 000, Sergeant et al., 1999, Le Freche et al., 2012), Tau-1 (1/5000, Merck Millipore), S199P (directed against the phospho-serine 199, 1/4000, Sergeant et al., 1999), Tau-Phospho S396 (directed against the phosphor-serine 396, 1/10000, Lifetechnologies), Tau-Phospho 404 (1/10 000, Lifetechnologies), 422 (clone 2H9, a homemade monoclonal antibody developed against a phospho-peptide containing the phosphorylated serine 422 residue of Tau, numbering according to the longest human brain Tau-441 isoform), AT8 (1/1000, Thermo Scientific), AT270 (1/2000, Thermo Scientific), AT100 (1/1000, Thermo Scientific). Neuron specific enolase (1/10 000), β-actin (1/5000) and β-tubulin (1/10 000) were from Sigma-Aldrich.

Cell Culture and Transfection

Human neuroblastoma cell line SKNSH-SY5Y cells expressing the human Tau isoform 412 (with the exon 2 and 10 encoding sequences) (or SY5Y-Tau46) was as previously described in Bretteville et al., 2009.

Drug Treatment

Neuroblastoma SKNSH-SY5Y cells expressing the human Tau isoform 412 (with the exon 2 and 10 encoding sequences) were treated with 10 μM of the hydrochloride salt of N-[3-(4-{3-[Bis(2-methylpropyl)amino]propyl}piperazin-1-yl)propyl]-1,2,3,4-tetrahydroacridin-9-amine (Example 6, hereinafter named "Compound I.HCl") which was diluted in the culture medium as described in Bretteville et al., 2009.

Animal Treatment

Wild-type C57BL/6J animals of 3 months were purchased at Charles Rivers Laboratories (France) and were allow to acclimate in the animal facility for at least one week before any treatment. Thy-Tau22 transgenic colonies (C57BL/6J genetic background) were obtained by crossing heterozygous Thy-Tau22 males with C57BL/6 WT females. Thy-Tau22 mouse transgenic line exhibits progressive neuron-specific Alzheimer Disease-like Tau pathology devoid of motor deficits. In this model, a progressive development of NFT is observed in the hippocampus and amygdala, which parallels behavioral impairments (Schindowski et al., 2006). Furthermorever, in the hippocampus, hyper- and abnormally phosphorylated Tau species accumulate within the somato-dendritic area (Schindowski et al., 2006).

All animals were housed in a pathogen-free facility at 5 to 6 animals per cage (Techniplast Cages 1284L). They had ad libitum access to food and water in a 12/12-hour light-dark cycle and maintained in constant temperature of 22° C.

For animal treatment, animals were randomly distributed and the compound of Formula I was given in the drinking water at final concentration of 0.5 or 1 mg/kg. Drinking bottles were changed once per week, volume consumption was measured along the treatment period. Food consumption and body weight were assessed. In wild-type animals the pilot study of drug treatment was performed for one month to establish the innocuousness of the treatment with the compound of Formula I. This was based on the physiological, social and behavioural assessments. Thy-Tau22 males were treated for 4 months starting at 3 month old. All protocols were approved by the local ethics committee (n° 342012, CEEA).

Spatial Memory Assessment Using Morris Water Maze

Before any behavioral test, exploratory and locomotion of treated and untreated animal were evaluated in a Open field (OF) 25 cm×25 cm arena. Four acquisitions in joined arena were performed simultaneously. Each mouse was placed in the arena and allowed to explore for at least 5 min. Parameters including distance, speed, velocity were acquired by video recording using the EthoVision video tracking equipment and software (Noldus, Information Technology, Paris, France) in a dedicated room. The anxiety, which could interfere with memory test, was evaluated by the elevated plus maze (EPM). Mice were placed in the centre of a plus-shaped maze consisting of two 10 cm wide open arms and two enclosed arms elevated at 50 cm from the floor. Locomotion, distance, speed and velocity were measured as well as the number of arm entries, time spent in the open versus closed arms, percentage of open arm entries and time per minute spent in the open arms on a total of 5 min test.

Morris Water Maze

Spatial learning and memory abilities were assessed in a standard hidden-platform acquisition and retention version of the Morris water maze task (Van der Jeugd et al., 2013). A 90-cm circular pool was filled with water opacified with nontoxic white paint and kept at 21° C. A 10-cm round rescue platform was hidden 1 cm beneath the surface of the water at a fixed position. Four positions around the edge of the tank were arbitrarily designated in order to divide it into four cardinal points (North, East, West and South) delineating four quadrants. This target quadrant contains the rescue platform, surrounded by to adjacent quadrant and a opposite quadrant. In the acquisition trial, each mouse was given four swimming trials per day with at least 10 min of intertrial interval, for four consecutive training days. The start position was pseudo-randomized across trials. Mice that failed to find the hidden platform within 2 min were manually positioned on the platform. They were allowed to remain on it for 15 s before putting them back to their cages. The time required to find the hidden rescue platform (escape latency) was used as a spatial learning index and was recorded using the Ethovision XT video tracking system (Noldus France). Swimming speed and total distance were also measured. 72 h after the acquisition phase, the hidden platform was removed and spatial memory was evaluated in a 60 s probe trial. The proportion of time spent in the target quadrant vs. the other quadrants was considered as a spatial memory index.

Mouse Brain Samples

After behavioral assessment, blood was collected in 1.5 mL polypropylene tubes (Eppendorf, France), mice were sacrificed by cervical dislocation to avoid any modifications instrumental to anesthesia (Lefreche et al. 2012). Hippocampi and cortices were dissected and snap frozen in 1.5 mL tubes (Eppendorf). Tissue was homogenized in Tris-HCl buffer (10 mM pH 7.4) containing 320 mM sucrose, protease inhibitors (Complete mini EDTA-free, Roche) sonicated and spun at 12,000×g for 10 min at 4° C. The supernatant was recovered, protein concentration was achieved using the BCA Protein quantification assay kit (Pierce) according to the manufacturer instruction. The supernatant was further processed for biochemical analyses or kept at −80° C. For 1D or 2D gels, the same lysis buffer was used. Thus, equal amount protein in Tris buffer were added with a solution containing 7M urea, 2M thiourée with 2% SDS and sonicated at 60 Hz 30 pulses.

1D SDS-PAGE and Western-Blotting

For the western-blot analysis of Tau proteins, SDS-PAGE was performed according to the manufacturer's instructions using Bis-Tris 4-12% gradient acrylamide gel (NuPage® Bis-Tris PreCast 12 wells, Life Technologies). The apparent molecular weights were calibrated using the molecular weight markers (Novex and Magic Marks, Life Technologies). Electrophoresis was performed under a continuous tension of 100V/per gel for 1 h. Proteins were reversibly stained with Ponceau Red to check the quality of the efficacy of protein transfer. For western-blotting, the membranes were blocked in 25 mM Tris-HCl pH 8.0, 150 mM NaCl, 0.1% Tween-20 (v/v) (TBS-T) and 5% (w/v) of skimmed milk (TBS-M) for 30 min and they were incubated overnight at 4° C. the primary antibody. The nitrocellulose membrane is rinsed three times by gentle shaking in TBS-T during 10 min each. The membrane was then incubated during 1 h at room temperature with secondary antibody (Peroxydase Labeled Anti-Rabbit IgG (H+L chains), Vector Laboratories). The immunoreactive complexes were revealed using the ECL™ Western Blotting kit and image acquisition was performed with the LAS-3000 Luminescence Image Analyser (FujiFilm Lifesciences) or exposed to Amersham Hyperfilm ECL™ (G&E healthcare). Digitized images were processed with ImageJ Software (NIH).

Two-Dimensional Gel Electrophoresis

Two-dimensional gel electrophoresis was performed according to the recently published procedure (Fernandez-Gomez et al., 2014). Briefly, cells were rinsed once with PBS and lysed in UTS buffer (7M urea, 2M thiourea, 2% SDS) and sonicated at 60 Hz 30 pulses. Lysate was precipitated with methanol/chloroform. 50 µg of proteins were precipitate using the chloroform/methanol procedure and the pellet was dissolved in 2D buffer [urea 7M, thiourea 2M, 4% CHAPS, and 0.6% Pharmalytes 3-10 (G&E Healthcare)]. Immobilized pH gradient strip 3-11 Immobiline™ DryStrip of 11 cm (G&E Healthcare) were rehydrated with 200 µL containing a final amount of 50 µg of protein and isoelectrofocusing was achieved with an IPGPhor III (G&E Healthcare) according to the manufacturer's instructions. The strips were layered onto a 4-12% Bis-Tris Poly-acrylamide Gel XT™ Precast Criterion (BioRad) and run with a constant tension of 100V as described for 1D SDS-PAGE. The Western blot was performed as above described for 1D SDS-PAGE and Western-blotting.

Quantification of Tau in Mouse Plasma hTau dosage was achieved using the total Tau and phospho-181 hTau Innotest® ELISA kits (Fujirebio Europe) according to the manufacturer's instructions. hTau or phospho-Tau dosage was performed using 25 or 75 µL of plasma.

Immunofluorescence

Neuroblastoma SY5Y-APPWT cells were plated in cell culture chamber slides (Labtek) and allowed to grow in DMEM supplemented with 10% Fetal calf serum. Treatment with compounds were performed following the same protocol described in the drug treatment paragraph. After 48 h, cells were fixed with 4% paraformaldehyde in 0.1 M phosphate buffer (PBS) for 15 min at room temperature. Cells were washed 3 times with ice cold PBS and blocked with PBS supplemented with 1% BSA. Antibodies were incubated overnight at 4° C. in PBS-BSA, rinsed 3-times with ice cold-PBS and incubated with a secondary FTIC or Rhodamine-conjugated secondary antibody (Lifesciences Technologies). The coverslips were mounted onto slides with Vectashield with DAPI mounting medium (Vector laboratories). Images were acquired with a Zeiss Apotome microscope or Leica confocal microscope. All data were analyzed using Photoshop Element 6 Software (Adobe) without any modification of raw images.

Immunohistochemistry

Serial coronal sections (n=3) of the same brain coordinates (George Paxinos et al.) were incubated with the phospho-dependent AT100 or AT8 antibodies. They respectively recognized phospho-epitope of tau at residues Thr 212-Ser 214 and Ser 202-Thr 205. Quantification of labeled neurons was achieved using the NIH-Image J software and expressed in arbitrary units (A.U).

Statistical Analyses

Results were reported as means±SEM. Differences between mean values were evaluated using the Student's t-test, one Way-ANOVA followed by a post-hoc Fisher's LSD test using GraphPad Prism 6 Software. P values <0.05 were considered significant.

Results

Modulatory Effect on Tau Phosphorylation and Tau Degradation

The effect of the compound of Formula I on Tau phosphorylation was analyzed in vitro and in vivo. Neuroblastoma SKNSH-SY5Y cells expressing the human Tau isoform 412 (with the exon 2 and 10 encoding sequences) were treated with 10 µM of the compound of Formula I.

In Vitro Experiments

Figure 1:
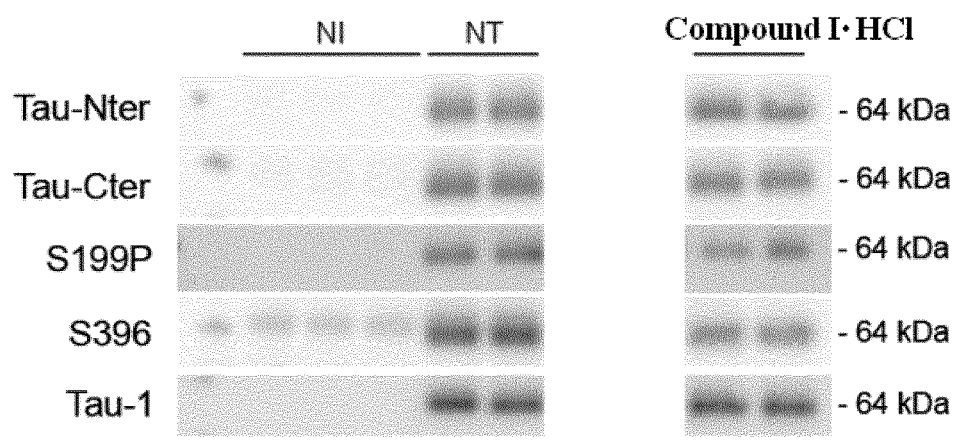
FIG. 1: Determination by 1D gel electrophoresis of the expression of the Tau protein by using Pan-Tau antibodies (Tau-Nter, Tau-Cter) and of the phosphorylation of the Tau protein by using phospho-dependent Tau antibodies (S199P, S396) and non-phosphorylated epitote comprised between 198-205 (Tau-1), in non-induced conditions (NI), induced but non-treated conditions (NT) and with administration of Compound I.HCl.
Figure 2:
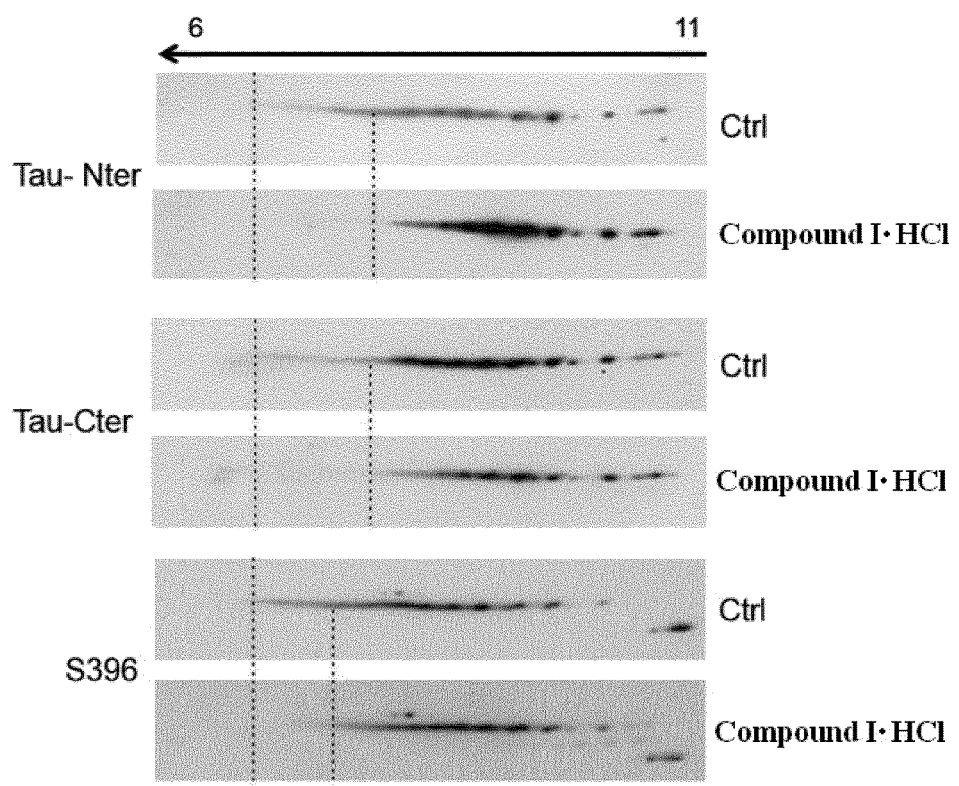
FIG. 2: Determination by 2D gel electrophoresis of the expression of the Tau protein by using Pan-Tau antibodies (Tau-Nter, Tau-Cter) and of the phosphorylation of the Tau protein by using phospho-dependent Tau antibody (S396), with an induced but non-treated condition (Ctrl) and with administration of Compound I.HCl.

Expression and total phosphorylation was assessed by 1D and 2D gel electrophoresis using phospho-dependent and pan-Tau antibodies (FIGS. 1 and 2). The phospho-dependant Tau antibody S199P is directed against the phosphorylated serine 199 residue (numbering according to the longest human Tau isoform) and is an early marker of Tau hyperphosphorylation during neurofibrillary degeneration (Maurage et al., 2003). The S396 antibody is directed to an epitope comprising the phosphorylated serine 396 of Tau (numbering according to the longest brain tau isoform of 441 amino acids). Tau expression is induced by tetracycline treatment and cells were treated afterwards with the compound of Formula I. Change of Tau expression or phosphorylation is compared to the induced but non-treated condition.

No significant change of Tau expression was observed with the compound of Formula I although Tau phosphorylation at serines 199 and 396 was reduced in cells treated with the compound of Formula I (FIG. 1).

These results were corroborated using 2D gel electrophoresis. In control conditions, isovariants of Tau were resolved between pI 6.5 and 10.5. Following treatment with the compound of Formula I, a reduction of the isovariants at the neutral pI was observed with Tau396 phospho-dependent antibody (S396) as well as with both N- and C-terminal directed pan-Tau antibodies (FIG. 2).

In Vivo Experiments

To further determine the effect of the compound of Formula I on Tau metabolism, wild-type C57/BL6 animals were treated with 0.5 and 1 mg/Kg of the compound of Formula I for 1 month and endogenous MAPT expression was assessed by 2D gel electrophoresis. Tau protein isovariants consist of three series ranging from pI 10 to 6. The major and most basic isovariants correspond to the mouse Tau isoform comprising the sole exon 10 encoding sequence. The two other series of isoforms of molecular weight of 64 and 69 kDa are isovariants of Tau isoforms which, in addition to the exon 10, contain exon 2 or exon 2+3 encoding sequences, respectively.

Figure 3:
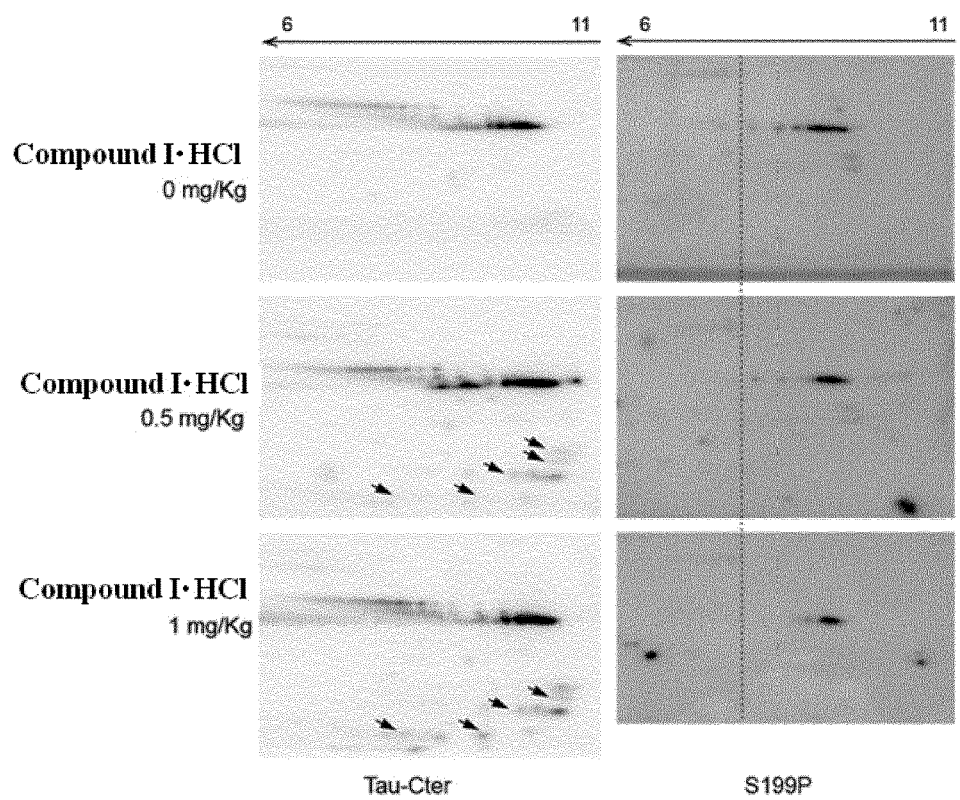
FIG. 3: Increase Tau C-terminal catabolites and reduce phosphorylation at serine 199. The 2D pattern of Tau proteins from the brain of WT animals treated with 0.5 mg/Kg or 1 mg/Kg was revealed a pan-Tau antibody (Tau-Cter) and a phospho-dependent antibody against the phosphorylated serine 199.

As shown at FIG. 3 with the Tau-Cter antibody, the distribution of Tau isovariants did not significantly change in treated animals although low molecular weight Tau catabolic products (indicated by arrows on FIG. 3) increased in number and intensity at 0.5 mg/Kg and even more significantly at 1 mg/Kg of the compound of Formula I.

Interestingly when the antibody S199 is used, 5 isovariants of Tau are detected in the non-treated condition and the number of isovariants stained diminished to 3 and 2 isovariants at both dosages (0.5 mg/Kg and 1 mg/Kg) of the compound of Formula I, respectively. The surface of the spots was also reduced suggesting a lower abundance of the phospho-site after treatment, although the overall 2D profile of the full-length Tau isoforms is preserved after treatment.

Altogether, these results suggest that the compound of Formula I modulates the endogenous Tau metabolism, in particular by reducing Tau phosphorylation and by increasing Tau proteolysis.

Preserved Spatial Memory and Reduced Tau Pathology in Thy-Tau22 Transgenic Animals The hippocampal development of NFT in Thy-Tau22 is correlated to an impairment of the spatial memory (Laurent et al., 2015). The spatial memory can be preserved by voluntary exercise (Belarbi et al, 2011) or immunotherapy (Troquier et al., 2012) thus making Thy-Tau22 a good model to test beneficial or detrimental effect of drugs. Thy-Tau22 mice were treated for 4 months with 0.5 mg/kg of Compound I.HCl and the spatial memory was assessed using the morris water maze.

Figure 4:
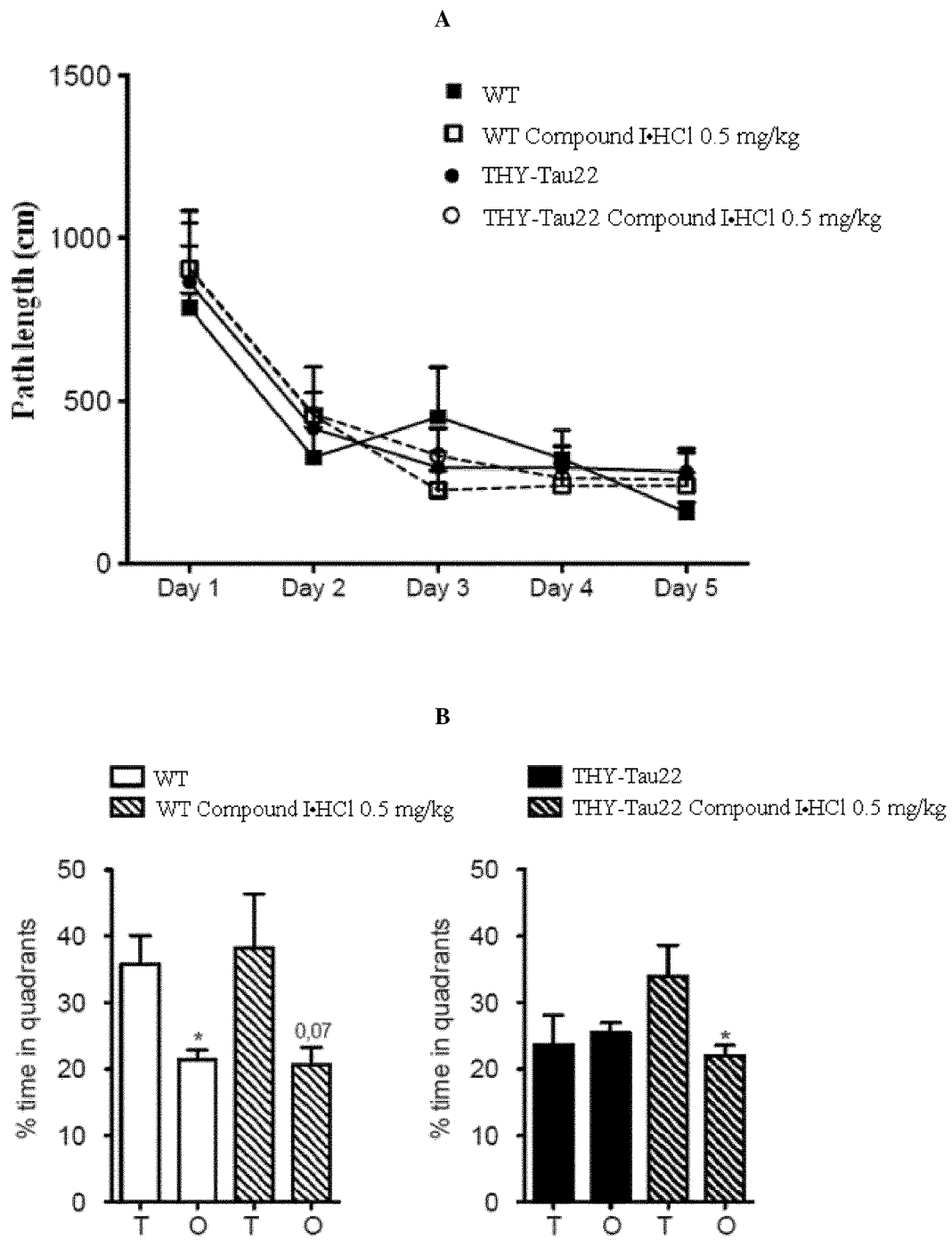
FIG. 4: Morris water maze evaluation of the spatial memory of Wild-type C57BL/6J animal (WT) and Thy-Tau22 mice, treated or not with 0.5 mg/Kg of Compound I.HCl.

As shown at FIG. 4A, the learning phase is not significantly different between the animal groups in the upper panel. After 5 days of learning, the distance to reach the platform is reduced showing that mice have successfully learnt. In the probe test, performed after 72 hours following the last learning day, the Compound of Formula I had no significant effect whereas in Thy-Tau22 mice the spatial memory was preserved.

In wild-type animals, the animal had a significant preference for the target quadrants than the three other quadrants independently of the treatment (FIG. 4B). Thus, the Compound of Formula I did not impact the cognitive performance of wild-type animals.

Thy-Tau22 animals spent equal % of time in the target quadrant (where the platform is positioned during the learning phase) versus the others. The lack of distinction is interpreted as a loss of spatial memory. In Thy-Tau22 treated animal, mice spent more time in the target quadrant and therefore showed a preserved spatial memory. The ANOVA statistical analysis showed that a treatment with the compound of Formula I protected or preserved the Thy-Tau22 mice from developing spatial memory impairments.

The burden of NFT in the hippocampal CA1 was investigated by immunohistochemistry and quantification. As mentioned above, AT100 recognizes pathological sites of Tau (residues Thr 212-Ser 214), and AT8 is used to detect the presence of phosphorylated tau (residues Ser 202-Thr 205). As shown at FIG. 5, the average surface of staining measured after AT100 staining was significantly reduced in Compound I.HCl treated animal whereas no significant differences were observed after AT8 immunostaining. AT100 recognized a pathological Tau epitope suggesting that Compound I.HCl impacts on the development of tau pathology but not necessarily on phosphorylated Tau proteins labeled by AT8.

To further assess this hypothesis, Tau expression and phosphorylation was further investigated by western-blotting (FIG. 6).

Brain proteins (of hippocampus) from untreated and Compound I.HCl treated thy-tau22 animals were resolved by 1D SDS-PAGE and Tau proteins were labeled with Pan-Tau antibodies (N-ter, C-ter). Catabolites detected with these antibodies are indicated as f-Nter and f-Cter. Phosphorylated variants of Tau were stained with the pSer199 (against phosphorylated serine 199), pSer262 (against the phosphorylated serine 262), pSer396 (against the phosphorylated serine 396), pSer404 (against the phosphorylated serine 404), pSer422 (against the phosphorylated serine 422) and Tau-1 (against unphosphorylated epitope comprised between amino acid residues 198-205). The quantification of each phospho-epitote is expressed as the ratio of phospho-epitope upon the Total hTau signal determined by the N-ter staining. This ratio is given as the % of variation to the control condition (untreated Thy-Tau22 animals) whose value is arbitrary given the value of 100%.

A significant reduction of Tau phosphorylation at phospho-sites 396 and 404 was observed whereas other phospho-sites were not significantly modified (FIG. 6). More interestingly, Tau C-terminal catabolites products at 43 kDa were significantly increased whereas the N-terminal catabolites were significantly decreased (FIG. 6). These results suggest that a treatment with the Compound I.HCl reduces the burden of Tau pathology by reducing the phosphorylation of Tau and increasing the catabolism of Tau which is sufficient to preserve the Thy-Tau22 animal model of neurofibrillary degeneration from development of spatial memory impairment.

REFERENCES

Belarbi K, Burnouf S, Fernandez-Gomez F J, Desmercières J, Troquier L, Brouillette J, Tsambou L, Grosjean M E, Caillierez R, Demeyer D, Hamdane M, Schindowski K, Blum D, Buée L. Loss of medial septum cholinergic neurons in THY-Tau22 mouse model: what links with tau pathology? Curr Alzheimer Res. 2011 September; 8(6):633-8.

Bretteville A1, Ando K, Ghestem A, Loyens A, Bégard S, Beauvillain J C, Sergeant N, Hamdane M, Buée L. Two-dimensional electrophoresis of tau mutants reveals specific phosphorylation pattern likely linked to early tau conformational changes. PLoS One. 2009; 4(3):e4843. doi: 10.1371/journal.pone.0004843.

Fernandez-Gomez F J, Jumeau F, Derisbourg M, Burnouf S, Tran H, Eddarkaoui S, Obriot H, Dutoit-Lefevre V, Deramecourt V, Mitchell V, Lefranc D, Hamdane M, Blum D, Buée L, Buée-Scherrer V, Sergeant N. Consensus brain-derived protein, extraction protocol for the study of human and murine brain proteome using both 2D-DIGE and mini 2DE immunoblotting. J Vis Exp. 2014 Apr. 10; (86). doi: 10.3791/51339.

Laurent C, Burnouf S, Ferry B, Batalha V L, Coelho J E, Baqi Y, Malik E, Mariciniak E, Parrot S, Van der Jeugd A, Faivre E, Flaten V, Ledent C, D'Hooge R, Sergeant N, Hamdane M, Humez S, Müller C E, Lopes L V, Buée L, Blum D. A2A adenosine receptor deletion is protective in a mouse model of Tauopathy. Mol Psychiatry. 2014 Dec. 2. doi: 10.1038/mp.2014.151.

Le Freche H, Brouillette J, Fernandez-Gomez F J, Patin P, Caillierez R, Zommer N, Sergeant N, Buée-Scherrer V, Lebuffe G, Blum D, Buée L. Tau phosphorylation and sevoflurane anesthesia: an association to postoperative cognitive impairment. Anesthesiology. 2012 April; 116(4):779-87. doi: 10.1097/ALN.0b013e31824be8c7.

Maurage C A, Sergeant N, Ruchoux M M, Hauw J J, Delacourte A. Phosphorylated serine 199 of microtubule-associated protein tau is a neuronal epitope abundantly expressed in youth and an early marker of tau pathology. Acta Neuropathol. 2003 February; 105(2):89-97.

Ryckebusch, A., Deprez-Poulain, R., Maes, L., Debreu-Fontaine, M.-A., Mouray, E., Grellier, P., Sergheraert, C. (2003) Synthesis and in Vitro and in Vivo Antimalarial Activity of N1-(7-Chloro-4-quinolyl)-1,4-bis(3-aminopropyl)piperazine Derivatives. J. Med. Chem. 46, 542-557.

Sergeant N, Wattez A, Delacourte A. Neurofibrillary degeneration in progressive supranuclear palsy and cortico-basal degeneration: tau pathologies with exclusively "exon 10" isoforms. J Neurochem. 1999 March; 72(3):1243-9.

Troquier L, Caillierez R, Burnouf S, Fernandez-Gomez F J, Grosjean M E, Zommer N, Sergeant N, Schraen-Maschke S, Blum D, Buée L. Targeting phospho-Ser422 by active Tau Immunotherapy in the THYTau22 mouse model: a suitable therapeutic approach. Curr Alzheimer Res. 2012 May; 9(4): 397-405.

Van der Jeugd A, Vermaercke B, Derisbourg M, Lo A C, Hamdane M, Blum D, Buée L, D'Hooge R. Progressive age-related cognitive decline in tau mice. J Alzheimers Dis. 2013; 37(4):777-88. doi: 10.3233/JAD-130110.

The invention claimed is:

1. A compound having Formula I

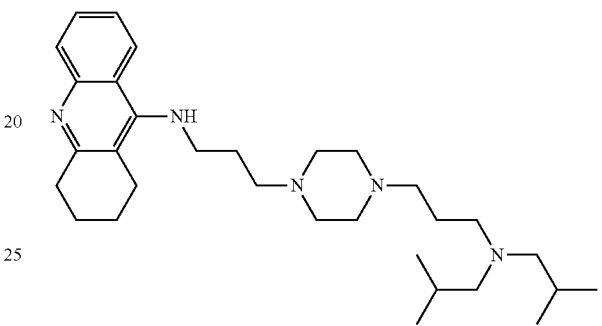

or a pharmaceutically acceptable salt thereof.

2. A pharmaceutical composition comprising a compound according to claim 1 or a pharmaceutically acceptable salt thereof and at least one pharmaceutically acceptable carrier, diluent, excipient and/or adjuvant.

* * * * *